United States Patent [19]

Arter et al.

[11] Patent Number: 5,474,907
[45] Date of Patent: Dec. 12, 1995

[54] MULTILAYER ANALYTICAL ELEMENT FOR SALICYLATE ASSAY

[75] Inventors: Thomas C. Arter, Rochester; Karen L. Warren; Harold C. Warren, III, both of Rush, all of N.Y.

[73] Assignee: Eastman Kodak Company, Rochester, N.Y.

[21] Appl. No.: 218,004

[22] Filed: Mar. 25, 1994

[51] Int. Cl.$^6$ .............................. C12Q 1/26; C12N 9/96; G01N 21/00
[52] U.S. Cl. .................... 435/25; 435/26; 435/28; 435/188; 435/805; 422/56; 422/57
[58] Field of Search ................... 435/25, 26, 28, 435/188, 805, 970; 422/56, 57; 436/170, 810; 530/362, 363; 536/17.9

[56] References Cited

U.S. PATENT DOCUMENTS

| | | | |
|---|---|---|---|
| 4,042,335 | 8/1977 | Clement | 23/253 TD |
| 4,144,306 | 3/1979 | Figueras | 422/56 |
| 4,416,983 | 11/1983 | Roder | 435/25 |
| 4,587,102 | 5/1986 | Nagatomo et al. | 422/56 |
| 5,185,249 | 2/1993 | Arter | 435/25 |
| 5,320,946 | 6/1994 | Daniel | 435/25 |

FOREIGN PATENT DOCUMENTS 875854  4/1978  Belgium.
392332A  4/1989  European Pat. Off..

OTHER PUBLICATIONS

Bertocchi P., A Flow-Through System for the Determination . . . Clin Chim Acta 207 (1992) pp. 205–213.
Ferry D., Binding of Valproic Acid to Protein Chem Abstracts 91: 68277e 1978.

*Primary Examiner*—Michael G. Wityshyn
*Assistant Examiner*—Ralph Gitomer

[57] ABSTRACT

A multilayer analytical element for measuring salicylate is disclosed. The element has a support. The support is coated with the following layers, top down to the support:

a) a spreading layer, b) a dye layer having a pH greater than 6.5 and comprising tyrosinase and a water-insoluble hydrazone coupling agent, c) a barrier layer that prevents passage of molecules having a molecular weight in excess of 5,000, and d) a reagent layer comprising salicylate hydroxylase and nicotinamide adenine dinucleotide (NADH), wherein the spreading layer comprises valproic acid, 8-anilino-1-naphthalenesutfonic acid (ANS) or the magnesium salt of 8-anilino-1-naphthalenesulfonic acid.

7 Claims, No Drawings

MULTILAYER ANALYTICAL ELEMENT FOR SALICYLATE ASSAY

FIELD OF THE INVENTION

This invention relates to clinical chemistry. It provides an analytical element for the assay of salicylate.

BACKGROUND OF THE INVENTION

The determination of salicylate in biological fluids such as human serum, has diagnostic significance. Acetylsalicylic acid (aspirin) is used as an analgesic and as an antiinflammatory drug for arthritis. It rapidly hydrolyzes to salicylate which has the therapeutic effect and a long half life. The therapeutic level as an analgesic is up to 20 mg/dl. For arthritis the level is up to 30 mg/dl. Problems such as headaches, tinnitus, flushing and hyperventilation occur at higher salicylate levels followed by imbalances in the acid-base level. Salicylate levels above 60 mg/dl can be lethal.

U.S. Pat. No. 4,416,983 discloses a solution method for the determination of salicylate in body serums. The method is based on the following 2 chemical reactions:

(1) salicylate + NAD(P)H + 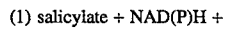

$$O_2 \xrightarrow{\text{salicylate hydroxylase (EC 1.14.13.1)}}$$

Pyrocatechol + $CO_2$ + $H_2O$ + NAD +

(2) pyrocatechol + hyrdazone + 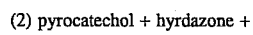

$$O_2 \xrightarrow{\text{tyrosinase (EC 1.10.3.1) or (EC 1.14.18.1)}}$$

colored material + $H_2O$

The method is carried out on a multilayer dry element disclosed in U.S. Pat. No. 5,185,249. The problem is that salicylate assay results are biased by the presence of albumin in serum samples. Albumin binds to salicylate thereby preventing its participation in the reaction described above. One approach to release salicylate from the albumin is to reduce sample pH. This is not possible in the dry test element disclosed in U.S. Pat. No. 5,185,249 because that element must also operate at the pH optimum of the enzymes used in the element.

SUMMARY OF THE INVENTION

The present invention provides a multilayer analytical element comprising a support coated in the following order, top down to the support:

a) a spreading layer, b) a dye layer having a pH greater than 6.5 and comprising tyrosinase and a water-insoluble hydrazone coupling agent, c) a barrier layer that prevents passage of molecules having a molecular weight in excess of 5,000, and d) a reagent layer comprising salicylate hydroxylase and nicotinamide adenine dinucleotide (NADH), wherein the spreading layer comprises a compound selected from the group consisting of valproic acid, 8-anilino-1-naphthalenesulfonic acid (ANS) and the magnesium salt of 8-anilino-1-naphthalenesulfonic acid.

The present invention greatly minimizes the salicylate binding bias encountered using the element described in U.S. Pat. No. 5,185,249. The reduced bias represents an unexpected improvement over the prior art particularly in view of the high bias encountered when 1) the assay is carried out on the element of the just mentioned patent and 2) valproic acid or ANS are added directly to serum.

With the above element the colored hydrazone catechol complex is easily measured because of its high extinction coefficient. The complex is sufficiently formed within 5 minutes to allow effective measurement of the salicylate concentration colorimetrically. Due to the physical separation of the salicylate hydroxylase from the hydrazone coupling agent, the element stability during storage is greatly lengthened and response is increased. The use of a $TiO_2$ pigmented spreading layer also reduces many spectral and turbity driven interferences seen in wet element systems.

In this element, the two reactions described above in U.S. Pat. No. 4,416,983, upon which the assay is based are carried out sequentially in separate layers of the element. The barrier layer does not allow passage of molecules having a molecular weight larger than 5,000. Salicylate hydroxylase has a reported molecular weight of 91,000. Thus it is trapped in the bottom layer below the barrier layer. The hydrazone coupling agent as a hydrochloride is water soluble, but at pH above 6.5, the hydrochloride is removed and the dye precipitates out of solution. In the analytical element of this invention, the hydrazone coupling agent is coated in an unbuffered gelatin layer at pH 5.5 over a pH 8 buffered barrier layer. Once coated and dried, the top barrier layer is also at a pH of 8, from buffer that has diffused up from the lower gelatin layer. As the pH increases, the 3-methyl-2-benzothiazolinone hydrazone hydrochloride (MBTH) drops out of solution and become crystalline in nature. In this form MBTH of the hydrazone coupling agent cannot diffuse down through the intervening barrier layer that separates it from salicylate hydroxylase.

The present invention also discloses a method for assaying biological fluids for salicylate comprising steps of:

a) spotting the analytical element described above with a sample suspected of containing salicylate;

b) allowing an incubation time up to 5 minutes or more; and c) making a colorimetric determination of the salicylate present in the sample.

DETAILED DESCRIPTION OF THE INVENTION

The element of this invention can be used to assay salicylate qualitatively or quantitatively in biological fluids in animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Elements of the invention can be configured in a variety of forms, including elongated tapes of any desired width, sheets, slides or chips, The elements can be used in manual or automated assay techniques. In general, in using the elements, salicylate determination is made by taking the element from a supply roll, chip packet or other source and physically contacting it with a sample (for example, up to 200 μl) of the liquid to be tested so that the sample and reagents interact sequentially within the element. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes or more, to facilitate color development. By incubation, we simply mean that the reagents are maintained in contact with each other for a period of up to 5 minutes or more before color measurements are made.

The dry analytical elements of this invention are multi-layered. At least one of the layers is preferably a porous spreading zone. The other layers include a reagent layer and a dye layer. The reagent layer includes a barrier zone and a reagent zone. All of the foregoing layers are coated on a support. The layers are generally in fluid contact with each other, meaning that fluids and reaction products (for example, color dyes) can pass or be transported between superposed regions of adjacent zones. Each layer can be separate or two or more zones can be separate areas in a single layer of the element. Besides the references noted above, suitable element components are described also, for example, in U.S. Pat. Nos. 4,042,335 (issued Aug. 16, 1977 to Clement), U.S. Pat. No. 4,132,528 (issued Jan. 2, 1979 to Eikenberry et al.), and U.S. Pat. No. 4,144,306 (issued Mar. 13, 1979 to Figueras).

Useful spreading layers can be prepared using fibrous materials, either mixed with a suitable binder material or woven into a fabric, as described in U.S. Pat. No. 4,292,272 (issued Sep. 29, 1981 to Kitajima et al.), polymeric compositions or particulate materials, for example a blush polymer such as disclosed in U.S. Pat. No. 3,992,158, beads bound together with or without binding adhesives, as described in U.S. Pat. Nos. 4,258,001 (issued Mar. 24, 1981 to Pierce et al.) and U.S. Pat. No. 4,430,436 (issued Feb. 7, 1984 to Koyama et al.) and Japanese Patent Publication 57(1982)-101760. Particularly useful spreading layers comprise barium sulfate or titanium dioxide. Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The layers can be coated on transparent supports such as poly(ethylene terephthalate). Other supports are well known in the art.

The elements of this invention can also contain one or more other addenda commonly put in the elements for various manufacturing or operational advantages. Such addenda include surfactants, buffers, solvents, hardeners and other materials known in the art. A typical element of the present invention is presented below.

| Element Structure and Content: | g/m² | Range g/m² |
|---|---|---|
| Spreading Layer | | |
| TiO₂ pigment | 50.0 | 20–100 |
| Estane 5715 | 2.5 | .2–10 |
| Cellulose acetate binder | 6.9 | 2–20 |
| Poly-(N-isopropylacryl-amide) binder | .4 | .05–2 |
| TX-405 surfactant | .6 | 0–4 |
| Oleyl PEG surfactant | .8 | 0–3 |
| 8-anilino-1-naphthalenesulfonic acids or valproic acid | 1.5 | .1–10 |

| Element Structure and Content: | g/m² | Range g/m² |
|---|---|---|
| Dye Layer | | |
| Gelatin binder | 6.0 | .2–15 |
| Sodium chloride | .5 | 0–4 |
| Bis(vinylsulfonylmethyl) ether hardener | .1 | .01–1 |
| 3-Methyl-2-benzothiazolinone hydrazone | .4 | .05–2 |
| Tyrosinase | 960 U/m² | 10–300,000 U/m² |
| pH | 5.2 | 3–6.5 |
| Reagent Layer | | |
| Barrier Zone | | |
| DI type IV gelatin binder | 6.0 | .2–15 |
| Bicine buffer | 1.5 | .2–5 |
| Sodium chloride | .5 | 0–4 |
| Bis(vinylsulfonylmethyl) ether | .1 | .02–1 |
| Nicotinamide adenine dinucleotide | 1.0 | .1–4 |
| pH | 7.8 | 6.5–9.0 |
| Reagent Zone | | |
| Gelatin binder | 6.0 | .2–15 |
| Bicine buffer | 1.5 | .2–5 |
| Sodium chloride | .5 | 0–4 |
| Bis(vinylsulfonylmethyl) ether | .1 | .02–1 |
| Salicylate hydroxylase | 576 U/m² | 100–5K |
| pH | 7.8 | 6.5–9.0 |
| Support: Poly(ethylene terephthalate) | | |

COMPARATIVE EXAMPLE

The approach involved in solving the problem of bias in salicylate determinations caused by the presence of albumin was to provide a compound that would displace salicylate from the albumin without causing other adverse effects on the assay. This was first explored by pretreating a patient sample with ANS or valproic acid. The pretreated sample was then spotted on the element of U.S. Pat. No. 5,185,249. In this test ANS or valproic acid were spiked into serum samples with constant salicylate levels, but varying albumin levels. Dry element recovery of the salicylate was then compared in Table I.

TABLE I

Recovery of Pretreated Samples
(Salicylate Prediction in mg/dL)

| | Albumin Level (g/dL) | | | |
|---|---|---|---|---|
| | 2g/dL | 5g/dL | 8g/dL | High-Low Bias |
| No Pretreatment Valproic acid | 45.3 | 40.2 | 35.0 | −10.3 |
| −10 mM/L | 45.3 | 42.2 | 38.3 | −7.0 |
| −25 mM/L | 43.2 | 41.9 | 38.5 | −4.7 |
| ANS | | | | |
| −10 mM/L | 43.9 | 41.9 | 38.4 | −5.5 |
| −25 mM/L | 45.0 | 43.3 | 40.7 | −4.3 |

This study showed that both valproic acid and 8-anilino-1-naphthalenesulfonic acid (ANS) can be added to patient samples to reduce albumin caused salicylate bias in assay conducted on the dry element of U.S. Pat. No. 5,185,249.

However, a large bias (10 percent prediction error) still exists at 25 millimolar concentration for both valproic acid and ANS. These results show that neither of these compounds eliminate salicylate bias in the element. Moreover, pretreatment of patient samples with either of these compounds adds an undesirable manual step to a now automated analytical operation.

Example 1

Assays for salicylate were carried out on the element of the invention presented above using ANS in the spreading layer. The results were then compared to the original element without ANS.

TABLE II

Recovery of Salicylate vs HPLC Reference Method
(Target Salicylate Level 25 mg/dL)

| Albumin Level (g/dL) | 1.7 | 2.5 | 3.2 | 3.7 | 4.2 | 4.7 | 5.4 |
|---|---|---|---|---|---|---|---|
| Element without ANS | 144% | 136% | 116% | 104% | 100% | 96% | 94% |
| Invention Element with ANS | 102% | 104% | 103% | 100% | 100% | 98% | 100% |

There is an almost complete elimination of the albumin-salicylate binding bias when ANS is present in the spreading layer. This is entirely unexpected in view of the fact that the use of 25 millimolar of ANS in the pretreatment method of the comparative example did not reduce salicylate bias sufficiently for assay purposes. One skilled in the art would expect better results with the pretreatment method since ANS should have more time and mobility to displace the salicylate from the albumin. Inclusion of ANS in the spreading layer of the element results in an unexpected improvement in bias compared to the expected marginal improvement one would have predicted from the pretreatment of serum with ANS.

Example 2

This improvement in performance shows up in general accuracy improvements in actual patient samples (which vary in albumin content) conducted on the element of this invention. Test results showed bias was reduced almost to zero in the serum concentration in the zone around 20 to 30 mg/dL of salicylate that contains many variations in albumin level. The improved element, with ANS in the spreading layer, almost eliminates the bias in this zone between the two methods.

Example 3

In this example, the element of the invention included 1.0 g/m2 of Valproic acid instead ANS. The following results were generated.

TABLE III

Recovery of Salicylate vs HPLC Reference Method
(Target salicylate level 25 mg/dL)

| | Albumin Level (g/dL) | | |
|---|---|---|---|
| | 2 g/dL | 6 g/dL | High-Low Bias |
| Element without valproic acid in spread layer | 132% | 95% | 9.7 mg/dL of Salicylate |
| Element with 1.0 g/m² Valproic acid in Spread layer | 119% | 98.6% | 3.1 mg/dL of Salicylate |

This example also shows the reduction in bias using the element of this invention compared to 1)an element without valproic acid in the spread layer and 2)to the lateral element plus valproic acid as a pretreatment step used in the pretreatment step of the comparative example.

The invention has been described in detail with particular reference to preferred embodiments thereof, but it will be understood that variations and modifications can be effected within the spirit and scope of the invention.

We claim:

1. A multilayer analytical element comprising a support coated in the following order, top down to the support:
   a) a spreading layer,
   b) a dye layer having a pH greater than 6.5 and comprising tyrosinase and a water-insoluble hydrazone coupling agent,
   c) a barrier layer that prevents passage of molecules having a molecular weight in excess of 5,000, and
   d) a reagent layer comprising salicylate hydroxylase and nicotinamide adenine dinucleotide (NADH), wherein the spreading layer comprises a compound selected from the group consisting of valproic acid, 8-anilino-1-naphthalenesulfonic acid (ANS) and the magnesium salt of 8-anilino-1-naphthalenesulfonic acid.

2. The element of claim 1, wherein the barrier layer is a hardened gelatin.

3. The element of claims 1 or 2, wherein the dye layer, the barrier layer and the reagent layer each comprise hardened gelatin.

4. The element of claims 1 or 2, wherein the spreading layer comprises barium sulfate.

5. The element of claims 1 or 2, wherein the spreading layer comprises titanium dioxide.

6. The element of claims 1 or 2, wherein the hydrazone coupling agent is 3-methyl2-benzothiazolinone hydrazone hydrochloride (MBTH).

7. The element of claim 6, wherein the pH of the barrier layer and the reagent layer is about 8.0.

* * * * *